United States Patent [19]

Collins et al.

[11] 4,060,691
[45] * Nov. 29, 1977

[54] 7-{3-HYDROXY-2-[4-HYDROXY-4-(LOWER ALKYL)-TRANS-1-OCTEN-1-YL]-5-OXOCYCLOPENT-1-YL}HEPTANOIC ACIDS AND ESTERS

[75] Inventors: Paul W. Collins, Deerfield; Raphael Pappo, Skokie, both of Ill.

[73] Assignee: G. D. Searle & Co., Chicago, Ill.

[*] Notice: The portion of the term of this patent subsequent to June 22, 1993, has been disclaimed.

[21] Appl. No.: 642,830

[22] Filed: Dec. 22, 1975

Related U.S. Application Data

[63] Continuation-in-part of Ser. No. 454,913, March 26, 1974, Pat. No. 3,965,143.

[30] Foreign Application Priority Data

Mar. 6, 1975 South Africa .................. 75/1391

[51] Int. Cl.$^2$ .......................... C07C 177/00
[52] U.S. Cl. .................. 560/121; 260/345.7 P; 260/345.8 P; 260/448.8 R; 260/514 D; 424/305; 424/317; 560/231; 542/426
[58] Field of Search ............... 260/468 D, 514 D, 69, 260/240 R, 345.7, 345.8, 448.8 R

[56] References Cited

U.S. PATENT DOCUMENTS

| 3,950,406 | 4/1976 | Floyd .......................... 260/514 |
| 3,965,143 | 6/1976 | Collins et al. ................. 260/468 |

OTHER PUBLICATIONS

Collins et al., Tet. Letters, 4217, (1975).

*Primary Examiner*—Robert Gerstl
*Attorney, Agent, or Firm*—Barbara L. Cowley; John J. McDonnell

[57] ABSTRACT

7-{3-Hydroxy-2-[4-hydroxy-4-(lower alkyl)-trans-1-octen-1-yl]-5-oxocyclopent-1-yl{heptanoic acids and esters, displaying valuable pharmacological properties, e.g., gastric anti-secretory, are produced by the reaction of a 7-(3-oxygenated-5-oxocyclopent-1-en-1-yl)heptanoic acid or ester with the appropriate organometallic reagent.

5 Claims, No Drawings

7-{3-HYDROXY-2-[4-HYDROXY-4-(LOWER ALKYL)-TRANS-1-OCTEN-1-YL]-5-OXOCYCLOPENT-1-YL}HEPTANOIC ACIDS AND ESTERS

This application is a continuation-in-part of our co-pending application Ser. No. 454,913, filed Mar. 26, 1974 now Pat. No. 3,965,143.

The present invention relates to novel 7-{3-hydroxy-2-[4-hydroxy-4-(lower alkyl)-trans-1-octen-1-yl]-5-oxocyclopent-1-yl}heptanoic acids and related compounds. More particularly, this invention provides new and useful compounds of the general formula

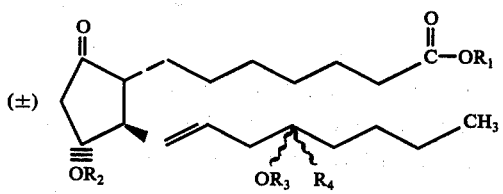

wherein $R_1$ is hydrogen or lower alkyl; $R_2$ and $R_3$ are hydrogen or a lower alkanoyl, tetrahydropyran-2-yl, or tri(lower alkyl)-silyl radical; $R_4$ is lower alkyl; and the wavy lines represent the alternative R or S configuration.

Particularly preferred compounds of the present invention are those of the formula

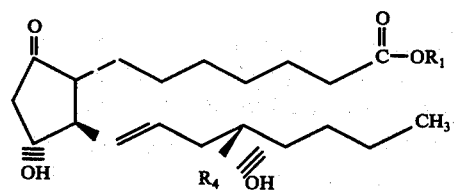

wherein $R_1$ and $R_4$ are defined as hereinbefore. These compounds display a markedly greater potency as gastric secretory inhibitors over the compounds disclosed in our copending application Ser. No. 454,913, filed Mar. 26, 1974. The compounds of formula (II) contain the particular stereochemistry of the naturally occurring prostaglandins, i.e., the four asymmetric carbon atoms which they contain are all of the same configuration as the naturally occurring prostaglandins.

The lower alkyl radicals represented in the foregoing structural formulas contain 1 to 6 carbon atoms and are typified by methyl, ethyl, propyl, butyl, pentyl, hexyl, and the branched-chain isomers thereof.

The lower alkanoyl radicals denoted in formula (I) are those containing 1 to 6 carbon atoms, i.e., formyl, acetyl, propionyl, butyryl, valeryl, caproyl, and the branched-chain radicals corresponding.

The novel compounds of the formula (I) wherein $R_2$ and $R_3$ are both hydrogen atoms display valuable pharmacological properties as is exemplified by their ability to inhibit the gastric secretion stimulated by secretogogues such as histamine and pentagastrin while furthermore possessing the surprising advantage of lacking the potent undesirable side-effects displayed by related substances. In addition, these compounds are inhibitors of blood platelet aggregation and, moreover, display anti-fertility and bronchodilating properties.

The specific assay used to detect gastric anti-secretory activity is described as follows:

Adult female beagle dogs weighing 13–20 kg. are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion, at the end of which time the test compound dissolved in an ethanolic isoosmotic phosphate buffer solution is administered by a single intravenous injection. The duration of the anti-secretory effects is determined and the side-effects, if any, recorded. The compound is rated active if statistically significant inhibition of secretory parameters occur following compound treatment.

Most surprisingly, it has been discovered that a single isomer, i.e., methyl 7-{3(R)-hydroxy-2β-[4(S)-4-hydroxy-4-methyl-trans-1-octen-1-yl]-5-oxocyclopent-1α-yl}heptanoate, of the previously known mixture, racemic methyl 7-}(3(R)-hydroxy-2β-[4(RS)-4-hydroxy-4-methyl-trans-1-octen-1-yl]-5-oxocyclopent-1α-yl}heptanoate, exhibits a potency greater than the expected four-fold potency of the mixture.

The compounds of formula (I) and (II) wherein $R_2$ and $R_3$ are alkanoyl, tetrahydropyran-2-yl or tri(lower alkyl)silyl radicals are useful intermediates for the synthesis of the compounds of formula (I) and (II) wherein $R_2$ and $R_3$ are both hydrogen atoms. The compounds of formula (I) wherein the wavy lines represent the R configuration also exhibit gastric anti-secretory activity.

Starting materials suitable for use in the manufacture of the compounds of the present invention are the 7-(3-oxygenated-5-oxocyclopent-1-yl)heptanoic acids and esters of the following formula

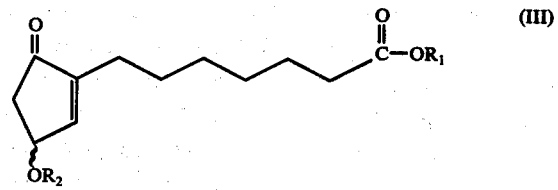

wherein $R_1$ and $R_2$ are defined as hereinbefore. Introduction of the oxygenated alkenyl side chain at the 2-position of the cyclopentane ring is effected by reaction with a suitable organometallic reagent. Particularly suitable reagents for introduction of the oxygenated alkenyl side chain are the alkenyl coppers and the lithium alkenyl cuprates prepared from the appropriate unsaturated alcohol. A convenient method for manufacture of the cuprate reagent comprises the reaction of an acetylenic alcohol of the following formula

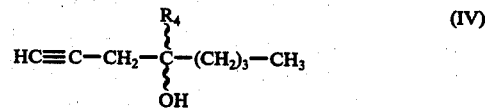

wherein $R_4$ and the wavy lines are as hereinbefore described, with a trialkylsilyl halide to afford the corresponding trialkylsilyl ether, contacting the resultant trialkylsilyl ether with 20% diisobutyl aluminum hydride to form a product which is reacted with iodine to yield the 1-alkenyl iodide, which is contacted with a cuprous acetylide and a lithium alkyl to afford the desired lithium cuprate reagent. The latter processes are exemplified by the reaction of 4(S)-4-methyl-1-octyn-4-ol with triethylsilyl chloride to afford 4(S)-4-methyl-1-octyn-4-ol triethylsilyl ether, reaction of that ether with 20% diisobutyl aluminum hydride, the product of which reaction is contacted with iodine to produce 4(S)-4-methyl-4-triethylsilyloxy-trans-1-octenyl iodide. That halide is then allowed to react with n-butyl lithium and cuprous 1-pentynylide, thus affording pure lithium [(1-pentynyl)-(4(S)-4-methyl-4-triethylsilyloxy-trans-1-octenyl)cuprate].

Alternatively, the 4(S)-4-methyl-4-triethylsilyloxy-trans-1-octenyl iodide may be prepared by contacting the 4(S)-4-methyl-1-octyn-4-ol triethylsilyl ether with catechol borane to yield 4(S)-4-methyl-4-triethylsilyloxy-trans-1-octenyl boronic acid which is then contacted with iodine to produce the desired iodide.

Reaction of the cuprate reagents with the aforementioned starting materials of formula (III), the manufacture of which compounds is detailed in Pappo and Jung U.S. Pat. No. 3,558,682, issued Jan. 26, 1971, results in introduction of the oxygenated alkenyl side chain at the 2-position of the cyclopentane ring. As a specific example, methyl 7-(3(R)-tetrahydropyran-2-yloxy-5-oxocyclopent-1-en-1-yl)heptanoate is allowed to react with lithium [(1-pentynyl)-(4(S)-4-methyl-4-triethylsilyloxy-trans-1-octenyl)cuprate], thus affording pure methyl 7-[3(R)-tetrahydropyran-2-yloxy-2β-(4(S)-4-methyl-4-triethylsilyloxy-trans-1-octen-1-yl)-5-oxocyclopent-1α-yl]heptanoate. Removal of the trialkylsilyl and tetrahydropyran-2-yl protecting groups is conveniently effected by reaction with acetic acid, thus producing pure methyl 7-[3(R)-hydroxy-2β-(4(S)-4-hydroxy-4-methyl-trans-1-octen-1-yl)-5-oxocyclopent-1α-yl]-heptanoate.

The starting materials of formula (III) and (IV) may be resolved prior to use in the above-described synthetic procedure, or used in their racemic forms. Use in their racemic forms results in the formation of isomeric mixtures. These mixtures are most conveniently separated by pressure liquid chromatography to give the desired optically active compounds.

Additional copper agents suitable for use in the manufacture of the instant compounds are the lithium divinyl cuprates and the vinyl coppers of the type described by Kluge et al., *J. Amer. Chem. Soc.*, 94, 7827 (1972), the lithium vinyl cyano cuprates of the type described by Gorlier et al., *Chem. Comm.*, 3, 88 (1973) and the lithium diorganocuprates as described by Mandeville et al., *J. Org. Chem.*, 39, 400 (1974).

The mono and/or di-acylated derivatives of the present invention are conveniently produced by reaction of the corresponding hydroxy substances with a lower alkanoic acid anhydride or halide, preferably in the presence of a suitable acid acceptor such as pyridine or triethylamine. As a specific example, the aforementioned pure methyl 7[3(R)-hydroxy-2β-(4(S)-4-hydroxy-4-methyl-trans-1-octen-1-yl)-5-oxocyclopent-1α-yl]hept-5-cis-enoate is contacted with acetic anhydride and pyridine, thus affording pure methyl 7-[3(R)-acetoxy-2β-(4(S)-4-acetoxy-4-methyl-trans-1-octen-1-yl)-5-oxocyclopent-1α-yl]heptanoate.

The manufacture of the acetylenic alcohols of formula (IV) is accomplished by reaction of the appropriate alkylbutylketone with hydrogen cyanide to afford the corresponding cyanoalcohol. This cyanoalcohol is hydrolyzed to afford the α-hydroxy acid of the formula

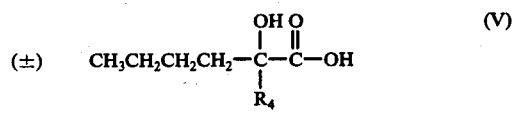

wherein $R_4$ is defined as hereinbefore. The compounds of formula (V) may be resolved at this stage to afford the optically pure enantiomer. The α-hydroxy acid is then reduced to the corresponding diol which is then contacted with tosyl or mesyl chloride to afford the tosylate or mesylate of the formula

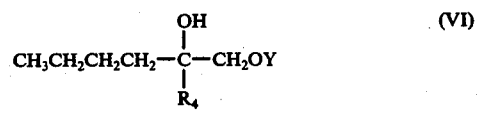

wherein $R_4$ is defined as hereinbefore and Y is a tosyl or mesyl radical. Alternatively, the OY group may be replaced by any other conventional leaving group, i.e., halogens such as bromo or iodo, or aroyl such as benzoyl, and used in the following reactions. This reaction sequence is illustrated by the reaction of 2-hexanone with hydrogen cyanide to afford 2-cyano-2-methylhexan-2-ol, which is hydrolyzed to 2-hydroxy-2-methylhexanoic acid. Optical resolution of this acid is accomplished using (+) or (−) 1-(1-naphthyl)ethylamine. Contacting of this resolved acid with lithium aluminum hydride affords the optically active 2-methylhexan-1,2-diol which, after contacting with tosyl chloride yields the 2-hydroxy-2-methylhexan-1-ol tosylate.

The compounds of formula (VI) may then be transformed into the appropriate compounds of formula (IV) by any of the various reaction sequences illustrated in Scheme 1.

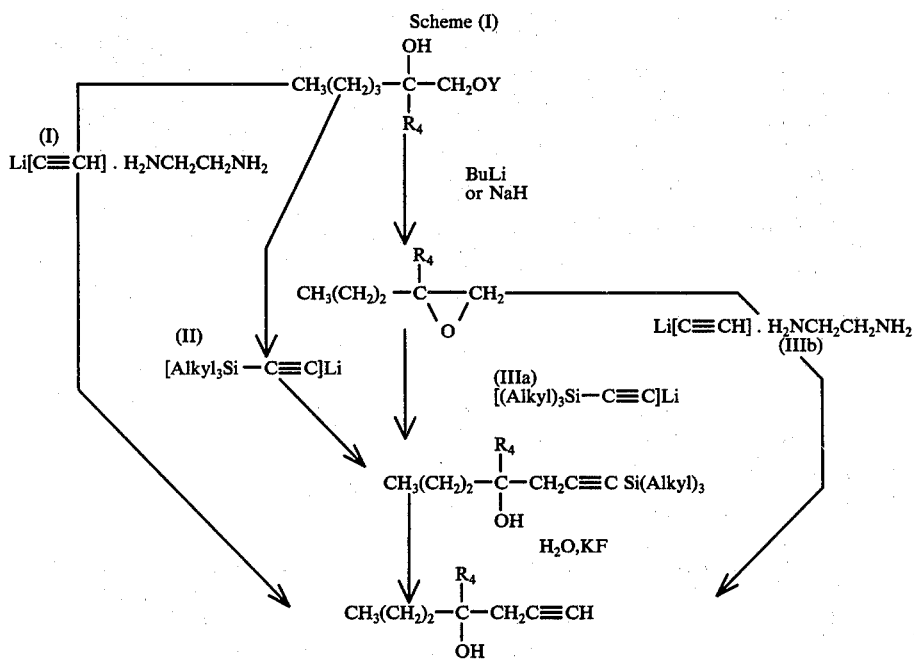

The reaction sequence denoted as (I) in Scheme (I) is exemplified by the reaction of the 2-hydroxy-2-methylhexan-1-ol tosylate with lithium acetylide-ethylenediamine in dimethylsulfoxide and tetrahydrofuran to directly yield 4-methyl-1-octyn-4-ol.

Alternatively, the 2-hydroxy-2-methylhexan-1-ol tosylate may be contacted with lithium trialkylsilyl acetylide to afford the 1-trialkylsilyl-4-methyl-1-octyn-4-ol which is then reacted with potassium fluoride in aqueous dimethylformamide to afford the desired 4-methyl-1-octyn-4-ol as shown by the reaction sequence (II) of Scheme (I).

Another useful synthetic procedure is illustrated by the reaction sequence (IIIa) of Scheme (I). The 2-hydroxy-2-methylhexan-1-ol tosylate is first contacted with n-butyl lithium or sodium hydride to afford the 2-butyl-2-methyloxirane. This compound is then reacted with a lithium trialkylsilyl acetylide to afford the 1-trialkylsilyl-4-methyl-1-octyn-4-ol which is then contacted with potassium fluoride in aqueous dimethylformamide to yield the product, 4-methyl-1-octyn-4-ol.

A fourth alternative procedure is typified by the formation of the 2-butyl-2-methyloxirane with n-butyl lithium or sodium hydride and reaction of this oxirane with lithium acetylide-ethylenediamine to directly produce the 4-methyl-1-octyn-4-ol as shown by reaction procedure (IIIb) of Scheme (I).

The reactions of Scheme (I) may be carried out with either the unresolved or the resolved optically active compounds of formula (VI). When the resolved material is used, there is obtained the pure, optically active, acetylenic alcohol in the final step since the conversion of the compounds of formula (VI) to the alcohols of formula (IV) does not affect the asymmetric center.

The invention will appear more fully from the examples which follow. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight unless otherwise noted.

EXAMPLE 1

A. A solution of 25.0 parts of 2-hexanone and 13.7 parts of sodium cyanide is stirred vigorously at 0° C. while adding dropwise 22.5 parts of nitric acid and 21 parts of ice. When the addition is completed, the resulting mixture is stirred at room temperature for 30 minutes. Then, the organic layer is separated and refluxed with 33 parts by volume of hydrochloric acid for 8 hours. This reaction mixture is stirred at room temperature for a further 18 hours, and the diluted with ethyl ether and water. The ether layer is separated, washed 4 times with water, dried over anhydrous sodium sulfate, and stripped to dryness under reduced pressure. The residue is distilled under reduced pressure to give, as a viscous oil, 2(RS)-2-hydroxy-2-methylhexanoic acid. This compound boils at 85°-88° C. at 0.2 - 0.35 mm. pressure and is represented by the following structural formula.

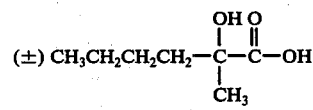

B. Repetition of the above procedure using an equivalent quantity of 3-heptanone affords 2(RS)-2-ethyl-2-hydroxyhexanoic acid.

EXAMPLE 2

A. 5.12 Parts of 2(RS)-2-hydroxy-2-methylhexanoic acid and 6.00 parts of (+)-1-(1-naphthyl)ethylamine are dissolved in 49 parts of dried and filtered ethyl ether. After standing for about 18 hours, a white crystalline precipitate forms. This precipitate is washed with a mixture of 222 parts tetrahydrofuran and 640 parts ethyl ether, filtered and dried to give the salt of 2(R)-2-hydroxy-2-methylhexanoic acid with (+)-1-(1-naphthyl)ethylamine. The salt is dissolved in methylene chloride and washed 4 times with portions of 1 N sulfuric acid to remove the amine. The resulting solution is dried over anhydrous sodium sulfate, filtered, and stripped in vacuo to afford a residue which is dissolved in ethyl ether and then filtered. Removal of the solvents affords 2(R)-2-hydroxy-2-methylhexanoic acid, which, after recrystallization from ethyl ether and n-hexane, melts at about 75° C., and exhibits an $[\alpha]_{365\,NM} = -24.8°$ (1.008% in water). This compound is represented by the following structural formula.

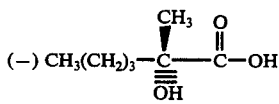

B. Repetition of the above procedure using an equivalent quantity of (−)-1-(1-naphthyl)ethylamine affords 2(S)-2-hydroxy-2-methylhexanoic acid, displaying an $[\alpha]_{365}^{25}{}_{NM} = +21.9°$ in water.

C. Substitution of an equivalent quantity of 2(RS)-2-ethyl-2-hydroxyhexanoic acid in the procedure detailed in the Paragraph B affords 2(S)-2-ethyl-2-hydroxyhexanoic acid.

EXAMPLE 3

A. To a solution of 2.10 parts lithium aluminum hydride in 71 parts of dried tetrahydrofuran is added dropwise over a 30 minute period a solution of 5.38 parts of 2(R)-2-hydroxy-2-methylhexanoic acid at 25°–35° C. The resulting solution is stirred at room temperature for an additional 30 minutes and then heated to reflux for a further 4 hours. The reaction mixture is cooled to about 10° C. and the remaining lithium aluminum hydride decomposed by the addition of aqueous tetrahydrofuran, 20% sodium hydroxide and water. After stirring until the pH is approximately 6.5, the precipitate is filtered off and washed with tetrahydrofuran. Removal of the solvent in vacuo affords a product which is distilled under high vacuum to give 2(R)-2-methylhexan-1,2-diol. This compound exhibits an $[\alpha]_{365}^{25}{}_{NM} = +12.1$ in chloroform and is represented by the following structural formula.

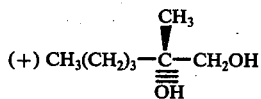

B. Repetition of the above procedure using 2(RS)-2-hydroxy-2-methylhexanoic acid or 2(S)-2-hydroxy-2-methylhexanoic acid affords 2(RS)-2-methylhexan-1,2-diol boiling at 99°–101° C. at 7 mm. pressure, or 2(S)-2-methylhexan-1,2-diol, respectively.

C. When the procedure detailed in the first paragraph is repeated using an equivalent quantity of 2(S)-2-ethyl-2-hydroxyhexanoic acid, there is obtained 2(S)-2-ethyl-hexan-1,2-diol.

EXAMPLE 4

A. 11.13 Parts of 2(RS)-2-methylhexan-1,2-diol is dissolved in 74 parts of dried pyridine and stirred in an ice-salt bath under a nitrogen atmosphere until it reaches a temperature of 0° C. Then, 19.25 parts of p-toluenesulfonyl chloride is added with stirring. After about 5 hours of stirring at 0°–3° C., the reaction mixture is decomposed by the addition of 35 parts of water, with cooling. Stirring is continued for a further 0.75 hour at room temperature at which time the reaction mixture is extracted with a mixture of benzene and ethyl ether. The organic layer is separated, washed once with cold 3 N hydrochloric acid, washed once with saturated sodium carbonate, and dried over anhydrous sodium sulfate. The resulting solution is filtered, stripped in vacuo to dryness, dissolved in ethyl ether, and stripped again to dryness to give, as an oil, 2(RS)-2-hydroxy-2-methylhexan-1-ol tosylate.

B. When equivalent quantities of 2(R)-2-methylhexan-1,2-diol or 2(S)-2-methylhexan-1,2-diol are substituted in the above procedure, there are obtained 2(R)-2-hydroxy-2-methylhexan-1-ol tosylate displaying an $[\alpha]_D^{25} = +0.7$ in chloroform, and 2(S)-2-hydroxy-2-methylhexan-1-ol tosylate, respectively.

C. Substitution of an equivalent quantity of 2(S)-2-ethylhexan-1,2-diol in the procedure of the first paragraph affords 2(S)-2-ethyl-2-hydroxyhexan-1-ol tosylate.

EXAMPLE 5

A. A solution of 1.48 parts of 2(RS)-2-hydroxy-2-methylhexan-1-ol tosylate and 1.43 parts of lithium acetylideethylenediamine dissolved in 8.9 parts tetrahydrofuran and 1.1 parts dimethylsulfoxide is stirred at room temperature for about 18 hours. Then the reaction mixture is decomposed by the addition of 5 parts water. After cooling, the mixture is acidified with 4.8 parts hydrochloric acid and extracted with ethyl ether. The ether extract is dried over anhydrous sodium sulfate, stripped to dryness in vacuo and distilled under reduced pressure to give 4(RS)-4-methyl-1-octyn-4-ol, boiling at 72°–74° C. at 14 mm. pressure. This compound is represented by the following structural formula.

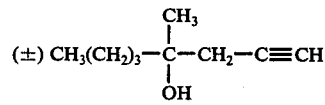

B. Substitution of equivalent quantities of 2(R)-2-hydroxy-2-methylhexan-1-ol tosylate or 2(S)-2-hydroxy-2-methyl-hex-1-ol in the above procedure affords 4(R)-4-methyl-1-octyn-4-ol displaying an $[\alpha]_{365}^{25}{}_{NM} = -5.5°$ in chloroform, and 4(S)-4-methyl-1-octyn-4-ol, respectively.

C. When an equivalent quantity of 2(S)-2-ethyl-2-hydroxyhexan-1-ol tosylate is substituted in the procedure of the first paragraph, there is obtained 4(S)-4-ethyl-1-octyn-4-ol.

EXAMPLE 6

A. To a solution of 0.46 part triethylsilylacetylene in 3 parts of ethyl ether is added 1.2 parts by volume of a 2.4 M n-butyl lithium in n-hexane solution at 0° C. After stirring for 30 minutes, 0.286 part of 2(RS)-2-hydroxy-2-methylhexan-1-ol tosylate is added. After a further stirring period, 1.1 parts of dimethylsulfoxide is added, and the mixture is stirred for 16 hours at room temperature. The reaction mixture is then poured into a mixture of ethyl ether and 1 N hydrochloric acid and shaken. The ether layer is separated, washed with water, dried over anhydrous sodium sulfate, and stripped under reduced pressure to give a mixture of 4(RS)-1-triethylsilyl-4-methyl-1-octyn-4-ol and 4(RS)-4-methyl-1-octyn-4-ol. Chromatography of the mixture on silica gel using a 10:90 mixture of ethyl acetate-n-hexane N-hexane as eluant affords the pure 4(RS)-4-methyl-1-octyn-4-ol.

B. When equivalent quantities of 2(R)-2-hydroxy-2-methylhexan-1-ol tosylate or 2(S)-2-hydroxy-2-methylhexan-1-ol tosylate are substituted in the above procedure, there are obtained 4(R)-4-methyl-1-octyn-4-ol, and 4(S)-4-methyl-1-octyn-4-ol, respectively, as well as their corresponding 1-triethylsilyl derivatives.

EXAMPLE 7

A. To an ethereal solution of 1.62 parts of sodium hydride (57% oil suspension) is added a solution of 10.02 parts of 2(RS)-2-hydroxy-2-methylhexan-1-ol tosylate in 35 parts of ethyl ether. Then, 5.5 parts of dried dimethylsulfoxide is added, with stirring, under nitrogen. The resulting mixture is heated to reflux and stirred thereat for 2 hours, whereupon heating is discontinued and the mixture allowed to stand at room temperature overnight. The reaction is decomposed by the addition of water. The aqueous layer is separated and extracted twice with ethyl ether. The ether extracts are combined, washed with water until neutral, and filtered. Removal of the solvent affords a residue which is purified by distillation to give 2(RS)-2-butyl-2-methyloxirane, boiling at 120°-126° C. This product is represented by the following structural formula.

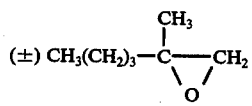

B. Substitution of equivalent quantities of 2(R)-2-hydroxy-2-methylhexan-1-ol tosylate or 2(S)-2-hydroxy-2-methylhexan-1-ol tosylate in the above procedure affords 2(R)-2-butyl-2-methyloxirane displaying an $[\alpha]_D^{25} = -13.8°$ in chloroform, or 2(S)-2-butyl-2-methyloxirane, respectively.

EXAMPLE 8

A. 5.37 Parts of 2(RS)-2-hydroxy-2-methylhexan-1-ol tosylate is dissolved in 43 parts of dried ethyl ether and the resulting solution cooled to −65° C. with stirring. A solution of 7.5 parts by volume of 2.5 N n-butyl lithium in n-hexane is added slowly over a twenty minute period. Upon completion of the addition, the cooling bath is removed and the mixture allowed to warm to room temperature. Stirring is continued for an additional 1 hour. After allowing the mixture to stand overnight in the cold, the resulting solid is filtered and washed with ethyl ether. The ether washings are combined with the filtrate and stripped in vacuo to dryness. The residue is distilled to afford 2(RS)-2-butyl-2-methyloxirane, boiling at about 122°-125° C.

B. When an equivalent quantity of 2(R)-2-hydroxy-2-methylhexan-1-ol tosylate or 2(S)-2hydroxy-2-methylhexan-1-ol tosylate is substituted for the 2(RS)-2-hydroxy-2-methylhexan-1-ol tosylate in the above procedure, there is obtained 2(R)-2-butyl-2-methyloxirane, or 2(S)-2-butyl-2-methyloxirane, respectively.

EXAMPLE 9

A. To a solution of 0.230 part of trimethylsilylacetylene in 3 parts of ethyl ether is added 0.9 part by volume of a 2.4 M solution of n-butyl lithium in n-hexane at 0° C. with stirring. After stirring at room temperature for an additional 15 minutes, 0.228 part of 2(RS)-2-butyl-2-methyloxirane and 1.1 parts dimethylsulfoxide are added. The resulting mixture is stirred overnight. The reaction mixture is diluted with ethyl ether, washed successively with dilute hydrochloric acid and water, dried over anhydrous sodium sulfate and stripped of solvent under reduced pressure. The residue is taken up in dimethylformamide and treated with potassium fluoride. The mixture is stirred for about 30 minutes at room temperature. It is then diluted with ether and washed five times with water, dried over anhydrous sodium sulfate and stripped of solvent in vacuo to give 4(RS)-4-methyl-1-octyn-4-ol, identical to the product obtained in Part A of Example 5.

B. Substitution of an equivalent quantity of 2(R)-2-butyl-2-methyloxirane or 2(S)-2-butyl-2-methyloxirane in the above procedure affords 4(R)-4-methyl-1-octyn-4-ol and 4(S)-4-methyl-1-octyn-4-ol, respectively.

EXAMPLE 10

A. 1.55 Parts of 2(RS)-2-butyl-2-methyloxirane are dissolved in 7.5 parts by volume of a mixture of 13 parts of tetrahydrofuran and 1.7 parts of dimethylsulfoxide. Then, 2.58 parts of lithium acetylide-ethylenediamine are added and the mixture is stirred under nitrogen at 65° C. for four hours. After standing overnight, 0.5 part water and 3 parts tetrahydrofuran is added with stirring. Then, 35 parts of ethyl ether and 6 parts concentrated hydrochloric acid are added successively, with stirring. The aqueous layer is separated, acidified and extracted three times with portions of ethyl ether. The ether extracts are combined, washed with water, dried over anhydrous sodium sulfate and filtered. The solvent is removed under reduced pressure to leave a residual yellow oil. Distillation under reduced pressure affords 4(RS)-4-methyl-1-octyn-4-ol, boiling at 66°-68° C. at 10 mm. pressure.

B. Repetition of the above procedure using an equivalent quantity of 2(R)-2-butyl-2-methyloxirane affords 4(R)-4-methyl-1-octyn-4-ol.

C. Substitution of an equivalent quantity of 2(S)-2-butyl-2-methyloxirane in the procedure detailed in Part A of this example yields 4(S)-4-methyl-1-octyn-4-ol.

EXAMPLE 11

A. A mixture consisting of 2.8 parts of 4(RS)-4-methyl-1-octyn-4-ol, 3.5 parts of triethylsilyl chloride, 10 parts by volume of dimethylformamide and 3 parts by volume of triethylamine is heated at the reflux temperature for about 16 hours, then is cooled and diluted with ether. That organic solution is then washed successively with dilute hydrochloric acid and water, dried over anhydrous sodium sulfate and the solvent removed under reduced pressure. Adsorption of the residue on a silica gel chromatographic column followed by elution with hexane affords 4(RS)-4-methyl-1-octyn-4-ol triethylsilyl ether, characterized by a nuclear magnetic resonance maximum at δ2.3.

B. To a solution of 1.27 parts of 4(RS)-4-methyl-1-octyn-4-ol triethylsilyl ether in 10 parts by volume of hexane is added, in a nitrogen atmosphere, at about 0° C; 4 parts of a 20% diisobutyl aluminum hydride solution in toluene. The resulting reaction mixture is allowed to stand at room temperature for about 16 hours, then is warmed at about 60° C. for 2 hours. After cooling, the solution is partially concentrated, then diluted with approximately 5 parts by volume of tetrahydrofuran and cooled to about 0° C. To that mixture is then added dropwise a solution consisting of 1.25 parts of iodine dissolved in 5 parts by volume of tetrahydrofuran. After the addition is complete, the mixture is partitioned between ether and hydrochloric acid. The ether layer is separated, washed successively with dilute aqueous sodium sulfite and water, then dried over anhydrous sodium sulfate and the solvent removed under reduced pressure. The resulting residue is purified by chromatography on a silica gel column using n-hexane as the eluant, to afford 4(RS)-4-methyl-4-triethylsilyloxy-trans-1-octenyl iodide. This compound is characterized by nuclear magnetic resonance spectrum peaks at about δ1.15 and δ5.95.

C. Substitution of an equivalent quantity of 4(S)-4-methyl-1-octyn-4-ol for the 4(RS)-4-methyl-1-octyn-4-ol and substantial repetition of the procedure detailed in Parts A and B above affords 4(S)-4-methyl-4-triethylsilyloxy-trans-1-octenyl iodide. This compound is characterized by nuclear magnetic resonance spectrum peaks at about δ1.15 and δ5.95.

D. When an equivalent quantity of 4(R)-4-methyl-1-octyn-4-ol is substituted in the procedure detailed in Parts A and B above, there is produced 4(R)-4-methyl-4-triethylsilyloxy-trans-1-octenyl iodide.

E. Substitution of an equivalent quantity of 4(S)-4-ethyl-1-octyn-4-ol for the 4(RS)-4-methyl-1-octyn-4-ol used in Parts A and B of this example, and substantial repetition of the procedure detailed therein affords 4(S)-4-ethyl-4-triethylsilyloxy-trans-1-octenyl iodide.

EXAMPLE 12

A mixture consisting of 0.24 part of methyl 7-(3(RS)-hydroxy-5-oxocyclopent-1-en-1-yl)heptanoate, 0.2 part of 2(S)-aminoxyisocaproic acid and 4 parts of methanol is treated with 0.5 parts of pyridine. The resulting mixture is allowed to stand at room temperature for about 16 hours, then is poured into a mixture consisting of 45 parts of ethyl acetate and 20 parts by volume of 0.5 N hydrochloric acid. The ethyl acetate layer is separated, washed with water and dried over anhydrous sodium sulfate. The solvent is removed by evaporation under reduced pressure and the residue is chromatographed on a silica gel column using 1% ethyl acetate in chloroform as the eluant, thus affording, successively, methyl 7-{3(R)-hydroxy-5-[(1-carboxyisoamyl)oxyimino]cyclopent-1-en-1-yl}heptanoate, melting at about 62°-63° C., and methyl 7-{3(S)-hydroxy-5-[(1-carboxyisoamyl)oxyimino]cyclopent-1-en-1-yl}heptanoate.

Each of the above oximes is mixed with 1.5 parts of ammonium acetate, 1 part of acetic acid, 10 parts of water, 27 parts of tetrahydrofuran and 3 parts by volume of an aqueous 20% titanium trichloride solution and stirred at 60° C. for about 16 hours under a nitrogen atmosphere. Each mixture is diluted with ether and extracted with water. The ether layer is separated, washed successively with aqueous 2% sodium bicarbonate and water, dried over anhydrous sodium sulfate and stripped of solvent under reduced pressure to yield, respectively, methyl 7-(3(R)-hydroxy-5-oxocyclopent-1-en-1-yl)heptanoate, represented by the following structural formula

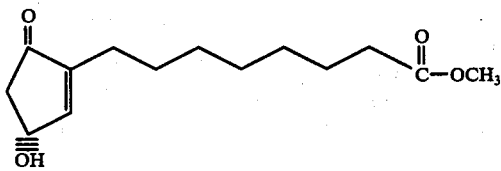

and methyl 7-(3(S)-hydroxy-5-oxocyclopent-1-en-1-yl)heptanoate, represented by the following structural formula.

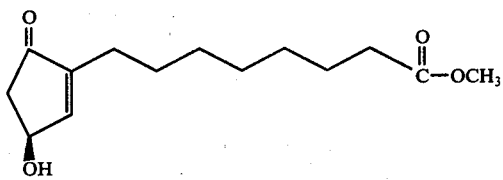

EXAMPLE 13

A. To a solution of 1.74 parts of methyl 7-(3(S)-hydroxy-5-oxocyclopent-1-en-1-yl)heptanoate in 12 parts by volume of dry benzene is added 0.005 part of p-toluenesulfonic acid and 1.74 parts of dihydropyran. The reaction mixture is stirred for 5 minutes under a nitrogen atmosphere and then allowed to stand at room temperature for a further 2 hours. The resulting solution is diluted with ethyl acetate, washed with water, dried over anhydrous sodium sulfate, and stripped of solvent under reduced pressure to afford methyl 7-(3(S)-tetrahydropyran-2-yloxy-5-oxocyclopent-1-en-1-yl)-heptanoate.

B. Substitution of an equivalent quantity of methyl 7-(3(R)-hydroxy-5-oxocyclopent-1-en-1-yl)heptanoate for the methyl 7-(3(S)-hydroxy-5-oxocyclopent-1-en-1-yl)heptanoate and substantial repetition of the procedure detailed above affords methyl 7-(3(R)-tetrahydropyran-2-yloxy-5-oxocyclopent-1-en-1-yl)heptanoate.

C. When an equivalent quantity of methyl 7-(3(RS)-hydroxy-5-oxocyclopent-1-en--yl)heptanoate is substituted for the methyl 7-(3(S)-hydroxy-5-oxocyclopent-1-en-1-yl)-heptanoate and the procedure detailed in Part A substantially repeated, there is obtained methyl 7-(3(RS)-tetrahydropyran-2-yloxy-5-oxocyclopent-1-en-1-yl)heptanoate.

EXAMPLE 14

To a solution of 5.58 parts of 4(S)-4-methyl-4-triethylsilyloxy-trans-1-octenyl iodide in 38 parts by volume ether, under a nitrogen atmosphere, is added, at −65° C., 5.70 parts by volume of a 2.56 M n-butyl lithium solution in hexane. The resulting mixture is stirred for about 30 minutes, at the end of which time a solution consisting of 6.66 parts of copper 1-pentynilide bis-hexamethylphosphorus triamide (prepared from copper 1-pentynilide and hexamethylphosphorus triamide) dissolved in 38 parts by volume of ether is added with stirring. Stirring is continued for an additional 20 minutes, at the end of which time a solution consisting of 2.35 parts of methyl 7-(3(R)-tetrahydropyran-2-yloxy-5-oxocyclopent-1en-1-yl)heptanoate dissolved in 19 parts by volume of ether is added dropwise. The resulting mixture is stirred at about −63° to −66° C. for approximately 2.5 hours. The reaction mixture is then partitioned between ether and cold dilute hydrochloric acid. The ether layer is separated, diluted with approximately 500 parts by volume of an ether-ethyl acetate mixture, washed once with water, filtered, dried over anhydrous sodium sulfate, and stripped of solvent by distillation under reduced pressure. The resulting residue is purified by chromatography on a silica gel column, using a 30:70 mixture of ethyl acetate and benzene as the eluant. Removal of the solvent from the eluant affords pure methyl 7[(3(R)-tetrahydropyran-2-yloxy)-2β-(4(S)-4- hydroxy-4-triethylsilyloxy-trans-1-octen-1-yl)-5-oxocyclopent-1α-yl]heptanoate.

A solution consisting of 0.85 part of the latter compound dissolved in 50 parts by volume of a 3:1:1 acetic acid:water:tetrahydrofuran mixture is allowed to stand at room temperature for about 16 hours, then is diluted with a 1:1 benzene-ether mixture. The resulting ether-benzene solution is washed several times with water, dried over anhydrous sodium sulfate, stripped of solvent under reduced pressure and purified by chromatography using 100% ethyl acetate as eluant. Removal of the solvent from the eluant affords pure methyl 7-[3(R)-hydroxy-2β-(4(S)-4-hydroxy-4-methyl-trans-1-octen-1-yl)-5-oxocyclopent-1α-yl]heptanoate. This compound is characterized by an $[\alpha]_D^{25} = -54°$ in methanol and is represented by the following structural formula.

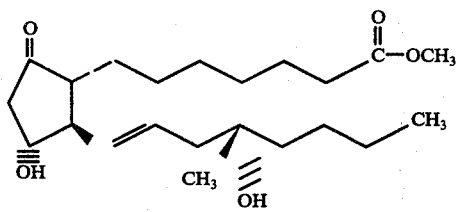

EXAMPLE 15

When an equivalent quantity of 4(R)-4-methyl-4-triethylsilyloxy-trans-1-octenyl iodide is substituted in the procedure of Example 14, there is produced pure methyl 7-[3(R)-hydroxy-2β-(4(R)-4-hydroxy-4-methyl-trans-1-octen-1-yl)-5-oxocyclopent-1α-yl]heptanoate characterized by an $[\alpha]_D^{25} = 55.5°$ in methanol. This compound is represented by the following structural formula.

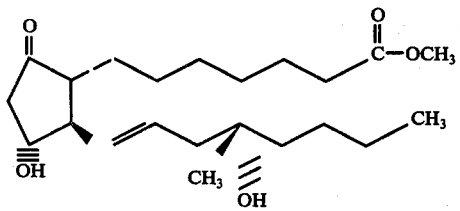

EXAMPLE 16

Substitution of an equivalent quantity of methyl 7-(3(S)-tetrahydropyran-2-yloxy-5-oxocyclopent-1-en-1-yl)heptanoate for the 7-(3(R)-tetrahydropyran-2-yloxy-5-oxocyclopent-1-en-1-yl)heptanoate used in Example 14, and substantial repetition of the procedure detailed therein affords pure methyl 7-[3(S)-hydroxy-2α-(4(S)-4-hydroxy-4-methyl-trans-1-octen-1-yl)-5-oxocyclopent-1β-yl]heptanoate. This compound is characterized by an $[\alpha]_D^{25} = +56.5°$ in methanol, and is represented by the following structural formula.

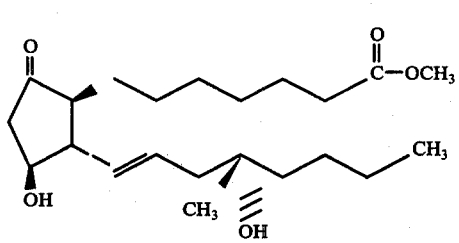

EXAMPLE 17

When equivalent quantities of 4(R)-4-methyl-4-triethylsilyloxy-trans-1-octenyl iodide and methyl 7-(3(S)-tetrahydropyran-2-yloxy-5-oxocyclopent-1-en-1-yl)heptanoate are substituted for the 4(S)-4-methyl-4-triethylsilyloxy-trans-1-octenyl iodide and methyl 7-(3(R)-tetrahydropyran-2-yloxy-5-oxocyclopent-1-en-1-yl)heptanoate, respectively, in the procedure of Example 14, there is obtained pure methyl 7-[3(S)-hydroxy-2α-(4(R)-4-hydroxy-4-methyl-trans-1-octen-1-yl)-5-oxocyclopent-1β-yl]heptanoate. This compound is characterized by an $[\alpha]_D^{25} = +47.5°$ in methanol and is represented by the following structural formula.

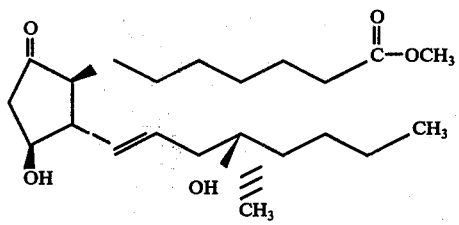

EXAMPLE 18

Substitution of an equivalent quantity of 4(S)-4-ethyl-4-triethylsilyl-trans-1-octenyl iodide for the 4(S)-4-methyl-4-triethylsilyloxy-trans-1-octenyl iodide used in Example 14, and substantial repetition of the procedure detailed therein affords methyl 7-[3(R)-hydroxy-2β-(4(S)-4-ethyl-4-hydroxy-trans-1-octen-1-yl)-5-oxocyclopent-1α-yl]heptanoate. This compound is represented by the following structural formula.

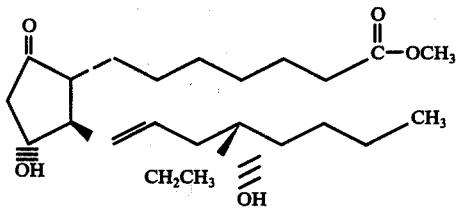

EXAMPLE 19

Substitution of equivalent quantities of 4(RS)-4-methyl-4-triethylsilyloxy-trans-1-octenyl iodide and methyl-7-(3(RS)-tetrahydropyran-2-yloxy-5-oxocyclopent-1-en-1-yl)-heptanoate in the procedure of Example 14 affords racemic methyl 7-[3(R)-hydroxy-2β-(4(RS)-4-hydroxy-4-methyl-trans-1-octen-1-yl)-5-oxocyclopent-1α-yl]heptanoate as a yellow oil characterized by nuclear magnetic resonance spectra at δ0.93, δ1.21 and δ4.07. This isomeric mixture is separated by high pressure liquid chromatography using DNA Bio-Gel HTP hydroxylapatite (Bio Rad Labs, Richmond, Calif.) as adsorbent to give racemic methyl 7-[(3(R)-hydroxy-2β-(4(S)-4-hydroxy-4-methyl-trans-1-octen-1-yl)-5-oxocyclopent-1α-yl]heptanoate and racemic methyl 7-[(3(R)-hydroxy-2β-(4(R)-4-hydroxy-4-methyl-trans-1-octen-1-yl)-5-oxocyclopent-1α-yl]heptanoate.

EXAMPLE 20

When an equivalent quantity of 4(RS)-4-methyl-4-triethylsilyloxy-trans-1-octenyl iodide is substituted for the 4(S)-4-methyl-4-triethylsilyloxy-trans-1-octenyl iodide in the procedure of Example 14, there is obtained 7-[3(R)-hydroxy-2β-(4(RS)-4-hydroxy-4-methyl-trans-1-octen-1-yl)-5-oxocyclopent-1α-yl]heptanoate.

This isomeric mixture is separated by high pressure liquid chromatography using DNA grade Bio-Gel HTP hydroxylapatite (Bio Rad Labs, Richmond, Calif.) as adsorbent, a 3.5:96.5 mixture of n-butanol-cyclohexane as eluant, and 77 lbs. pressure to give successively, the pure methyl 7-[3(R)-hydroxy-2β-(4(R)-4-hydroxy-4-methyl-trans-1-octen-1-yl)-5-oxocyclopent-1α-yl]heptanoate, identical to the product of Example 15, and pure methyl 7-[3(R)-hydroxy-2α-(4(S)-4-hydroxy-4-methyl-trans-1-octen-1-yl)-5-oxocyclopent-1α-yl]-heptanoate, identical to the product of Example 14.

EXAMPLE 21

A mixture consisting of 25 parts of methyl 7-[3(R)-hydroxy-2β-(4(S)-4-hydroxy-4-methyl-trans-1-octen-1-yl)-5-oxocyclopent-1α-yl]heptanoate, 10 parts of acetic anhydride and 10 parts of pyridine is allowed to stand at room temperature for about 16 hours, then is poured carefully into cold aqueous citric acid. The resulting aqueous mixture is allowed to stand at room temperature for about 1 hour, then is extracted several times with ether. The combined ether extracts are washed with cold water, dried over anhydrous sodium sulfate and concentrated under reduced pressure. The resulting residue is purified by adsorption on a silicic acid chromatographic column followed by elution with ethyl acetate in benzene, thus affording pure methyl 7-[3(R)-acetoxy-2β-(4(S)-4-acetoxy-4-methyl-trans-1-octen-1-yl)-5-oxocyclopent-1α-yl]heptanoate. This compound is represented by the following structural formula.

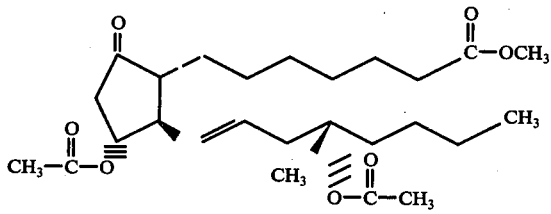

EXAMPLE 22

To a solution of 0.238 part of methyl 7-(3(RS)-hydroxy-5-oxocyclopent-1-en-1-yl)heptanoate in 4 parts by volume of methanol is added a solution consisting of 0.04 parts of sodium hydroxide in 1 part of water and the resulting reaction mixture is allowed to stand, in an atmosphere of nitrogen, at 0°-5° C. for about 16 hours. At the end of that time the reaction mixture is acidified by the addition of 1.1 parts by volume of 1 N hydrochloric acid, then is concentrated to a small volume at room temperature under reduced pressure. Extraction of that acidic mixture with ethyl acetate affords an organic solution, which is washed with aqueous sodium chloride, dried over anhydrous sodium sulfate and evaporated to dryness under reduced pressure, thus affording the crude product. Purification of that substance is effected by adsorption on a silicic acid chromatographic column followed by elution with ethyl acetate in benzene, thus affording 7-(3(RS)-hydroxy-5-oxocyclopent-1-en-1-yl)heptanoic acid.

EXAMPLE 23

When the resolved free acids of the compounds prepared in Example 13 are desired, the procedure of Example 13, first paragraph, is repeated to yield the resolved 3(R)- and 3(S)- hydroxy oxime esters. The resolved, separated oxime esters are then hydrolyzed according to the procedure detailed in Example 22 to yield pure 7-(3(R)-hydroxy-5-oxocyclopent-1-en-1-yl)heptanoic acid and pure 7-(3(S)-hydroxy-5-oxocyclopent-1-en-1-yl)heptanoic acid.

EXAMPLE 24

To a solution of 1.70 parts of 7-(3(R)-hydroxy-5-oxocyclopent-1-en-1-yl)heptanoic acid in 12 parts by volume of dry benzene is added 0.005 part of p-toluenesulfonic acid and 3.40 parts of dihydropyran. The reaction mixture is allowed to stand at room temperature for about 24 hours. The resulting solution is diluted with ethyl acetate, washed with water, dried over anhydrous sodium sulfate, and stripped of solvent under reduced pressure to afford tetrahydropyran-2-yl 7-(3(R)-tetrahydropyran-2-yloxy-5-oxocyclopent-1-en-1-yl)-heptanoate. This compound is represented by the following structural formula.

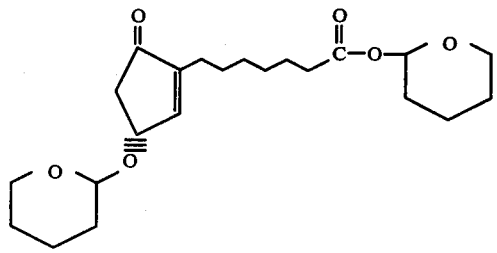

EXAMPLE 25

A solution of 1.85 parts of 4(S)-4-methyl-4-triethylsilyloxy-trans-1-octenyl iodide in 10 parts by volume of ether is cooled to about −60° C. and 2.33 parts by volume of a 2.14 M n-butyl lithium in hexane solution is added. That mixture is stirred for about 30 minutes, at the end of which time a solution of copper 1-pentynylide bis-hexamethylphosphorus triamide (prepared from 0.65 part of pentynyl copper and 1.63 parts of hexamethylphosphorus triamide) in 5 parts by volume of ether is added. The resulting mixture is stirred at −60° C. for 10 minutes and a solution of 0.75 part of tetrahydropyran-2-yl 7-(3(R)-tetrahydropyran-2-yloxy-5-oxocyclopent-1-en-1-yl)-heptanoate in 3 parts by volume of ether is added. That mixture is stirred first at −60° C. for 1 hour, then at −20° C. for an additional hour, then is diluted with ether. The ether solution is washed successively with dilute hydrochloric acid and water, then concentrated to dryness under reduced pressure. The residue is extracted with a 3:1:1 mixture of acetic acid:tetrahydrofuran:water and the extract is allowed to stand at room temperature for about 16 hours, then is diluted with ether and extracted with 5% aqueous potassium carbonate. The alkaline extract is washed with ether, acidified with dilute hydrochloric acid and extracted with ether. The resulting ether solution is washed with water, dried over anhydrous sodium sulfate and stripped of solvent under reduced pressure to afford, after chromatography, 7-[(3(R)-hydroxy-2β-(4(S)-4-hydroxy-4-methyl-trans-1-octen-1-yl)5-oxocyclopent-1α-yl]-heptanoic acid, represented by the following structural formula.

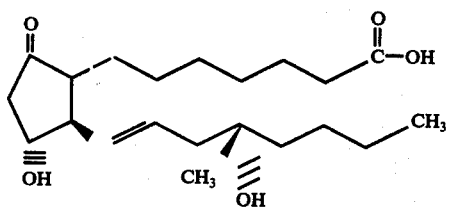

What is claimed is:

1. A compound of the formula

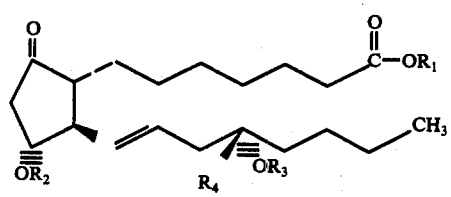

wherein $R_1$ is hydrogen or lower alkyl; $R_2$ and $R_3$ are hydrogen or a lower alkanoyl, tetrahydropyran-2-yl, or tri(lower alkyl)-silyl radical; and $R_4$ is a lower alkyl radical.

2. The compound according to claim 1 of the formula

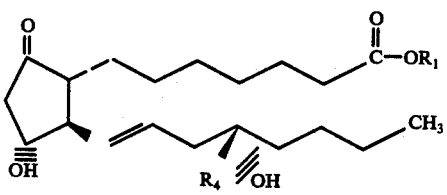

wherein $R_1$ is hydrogen or lower alkyl; and $R_4$ is a lower alkyl radical.

3. The compound according to claim 1 which is methyl 7-[(3(R)-hydroxy-2β-(4(S)-4-hydroxy-4-methyl-trans-1-octen-1-yl)-5-oxocyclopent-1α-yl]heptanoate.

4. The compound which is racemic methyl 7-[(3(R)-hydroxy-2β-(4(S)-4-hydroxy-4-methyl-trans-1-octen-1-yl)-5-oxocyclopent-1α-yl]heptanoate.

5. The compound which is methyl 7-[(3(R)-hydroxy-2β-(4(RS)-4-hydroxy-4-methyl-trans-1-octen-1-yl)-5-oxocyclopent-1α-yl]heptanoate.

* * * * *